(12) United States Patent
Meriac

(10) Patent No.: US 12,086,253 B2
(45) Date of Patent: Sep. 10, 2024

(54) ATTESTATION OF PROCESSING

(71) Applicant: Arm IP Limited, Cambridge (GB)

(72) Inventor: Milosch Meriac, Cambridge (GB)

(73) Assignee: Arm IP Limited, Cambridge (GB)

( * ) Notice: Subject to any disclaimer, the term of this patent is extended or adjusted under 35 U.S.C. 154(b) by 787 days.

(21) Appl. No.: 17/048,744

(22) PCT Filed: May 8, 2019

(86) PCT No.: PCT/GB2019/051267
§ 371 (c)(1),
(2) Date: Oct. 19, 2020

(87) PCT Pub. No.: WO2019/239095
PCT Pub. Date: Dec. 19, 2019

(65) Prior Publication Data
US 2021/0240830 A1    Aug. 5, 2021

(30) Foreign Application Priority Data

Jun. 13, 2018    (GB) ..................... 1809675

(51) Int. Cl.
*G06F 21/57*    (2013.01)
*G06F 9/455*    (2018.01)
(Continued)

(52) U.S. Cl.
CPC .......... *G06F 21/57* (2013.01); *G06F 9/45558* (2013.01); *G06F 21/64* (2013.01);
(Continued)

(58) Field of Classification Search
CPC . H04L 63/1433; H04L 63/20; H04L 63/1441; H04L 63/102; H04L 63/08;
(Continued)

(56) References Cited

U.S. PATENT DOCUMENTS 9,774,578 B1 *  9/2017  Ateniese ............... G06F 3/0673
11,258,612 B2 *  2/2022  Li ....................... G06Q 20/3829
(Continued)

FOREIGN PATENT DOCUMENTS

| CN | 105095773 | 11/2015 |
| WO | 2014/040411 | 3/2014 |

OTHER PUBLICATIONS

International Search Report and Written Opinion of the ISA for PCT/GB2019/051267, mailed Aug. 1, 2019, 16 pages.
(Continued)

*Primary Examiner* — Sharif E Ullah
(74) *Attorney, Agent, or Firm* — NIXON & VANDERHYE P.C.

(57) ABSTRACT

There is provided a data processing apparatus that includes an input policy filter that receives input data and an input provenance that relates to the input data. The filter forwards some or all of the input data and the input provenance according to at least one input policy. A processing environment receives the input data forwarded by the input policy filter and processes the input data to generate output data. A management environment produces an attestation of the processing environment and produces an output provenance based on the input provenance and the attestation. An output policy filter receives the output data and the output provenance and forwards the output data and the output provenance according to at least one output policy.

29 Claims, 11 Drawing Sheets

(51) Int. Cl.
  *G06F 21/64* (2013.01)
  *H04L 9/32* (2006.01)
  *G06Q 30/018* (2023.01)
  *G16H 40/20* (2018.01)
  *G16H 40/67* (2018.01)

(52) U.S. Cl.
  CPC .......... *H04L 9/3236* (2013.01); *H04L 9/3247* (2013.01); *G06F 2009/45587* (2013.01); *G06F 2221/034* (2013.01); *G06Q 30/018* (2013.01); *G16H 40/20* (2018.01); *G16H 40/67* (2018.01)

(58) Field of Classification Search
  CPC . H04L 63/10; H04L 2209/38; H04L 63/1416; H04L 2209/46; H04L 2209/805; H04L 41/046; H04L 41/0893; H04L 41/12; H04L 41/145; H04L 41/16; H04L 63/0853; H04L 63/104; H04L 63/1425; H04L 63/205; H04L 63/0272; H04L 61/1511; H04L 63/0236; H04L 67/563; G06F 2221/2101; G06F 21/552; G06F 21/554; G06F 21/56; G06F 21/566; G06F 2221/034; G06F 21/57; G06F 21/577; G06F 21/602; G06F 21/6209; G06F 21/6218; G06F 8/61; H04W 12/06; H04W 12/08; H04W 12/0027; H04W 12/00505; H04W 12/0609

USPC ............ 726/1, 2, 21, 36; 713/150, 163, 181; 380/255, 264, 276
  See application file for complete search history.

(56) References Cited

U.S. PATENT DOCUMENTS

| | | | |
|---|---|---|---|
| 2014/0096182 A1* | 4/2014 | Smith | ................. H04L 63/0853 726/1 |
| 2015/0082045 A1 | 3/2015 | D'Souza et al. | |
| 2017/0024568 A1 | 1/2017 | Pappachan et al. | |
| 2017/0024570 A1* | 1/2017 | Pappachan | ............ G06F 21/602 |
| 2018/0367533 A1* | 12/2018 | Ellingson | ............ H04L 63/0823 |
| 2019/0230129 A1* | 7/2019 | Digiambattista | ... H04L 63/1441 |
| 2019/0356674 A1* | 11/2019 | Irazabal | ................ H04L 63/102 |

OTHER PUBLICATIONS

Combined Search and Examination Report for GB1809675.0, dated Dec. 21, 2018, 5 pages.

Ko et al., "TrustCloud : A Framework for Accountability and Trust in Cloud Computing", 2011 IEEE World Congress on Services, Jul. 4, 2011, pp. 584-588.

Office Action for CN Application No. 201980037515.X issued Jan. 25, 2024 and English translation, 39 pages.

Office Action for CN Application No. 201980037515.X issued Jun. 22, 2024 and English translation, 39 pages.

* cited by examiner

ATTESTATION OF PROCESSING

This application is the U.S. national phase of International Application No. PCT/GB2019/051267 filed 8 May 2019, which designated the U.S. and claims priority to GB Patent Application No. 1809675.0 filed 13 Jun. 2018, the entire contents of each of which are hereby incorporated by reference.

The present technique relates to data processing.

In some systems, a number of predesigned modules are interconnected in order to produce a larger system. However, in such a system, it may be desirable to control the flow of data between modules. For instance, it might be desirable to control the nature and way in which data is received as well as controlling what happens to data once it has been processed, so as to provide security and privacy.

Viewed from a first example configuration, there is provided a data processing apparatus comprising: an input policy filter to receive input data and an input provenance that relates to the input data, and to forward some or all of the input data and the input provenance according to at least one input policy; a processing environment to receive the input data forwarded by the input policy filter and to process the input data to generate output data; a management environment to produce an attestation of the processing environment and to produce an output provenance based on the input provenance and the attestation; and an output policy filter to receive the output data and the output provenance and to forward the output data and the output provenance according to at least one output policy.

Viewed from a second example configuration, there is provided a method of data processing comprising: receiving input data and an input provenance that relates to the input data; forwarding some or all of the input data and the input provenance at an input policy filter according to at least one input policy; receiving the input data forwarded by the input policy filter; processing the input data to generate output data; producing an attestation of the processing environment; producing an output provenance based on the input provenance and the attestation; and receiving the output data and the output provenance and forwarding the output data and the output provenance according to at least one output policy.

Viewed from a third example configuration, there is provided a data processing apparatus comprising: means for receiving input data and an input provenance that relates to the input data; means for forwarding some or all of the input data and the input provenance according to at least one input policy; means for receiving the input data forwarded by the means for forwarding; means for processing the input data to generate output data; means for producing an attestation of the processing environment; means for producing an output provenance based on the input provenance and the attestation; and means for receiving the output data and the output provenance and forwarding the output data and the output provenance according to at least one output policy.

The present technique will be described further, by way of example only, with reference to embodiments thereof as illustrated in the accompanying drawings, in which:

Before discussing the embodiments with reference to the accompanying figures, the following description of embodiments and associated advantages is provided.

Figure 9:
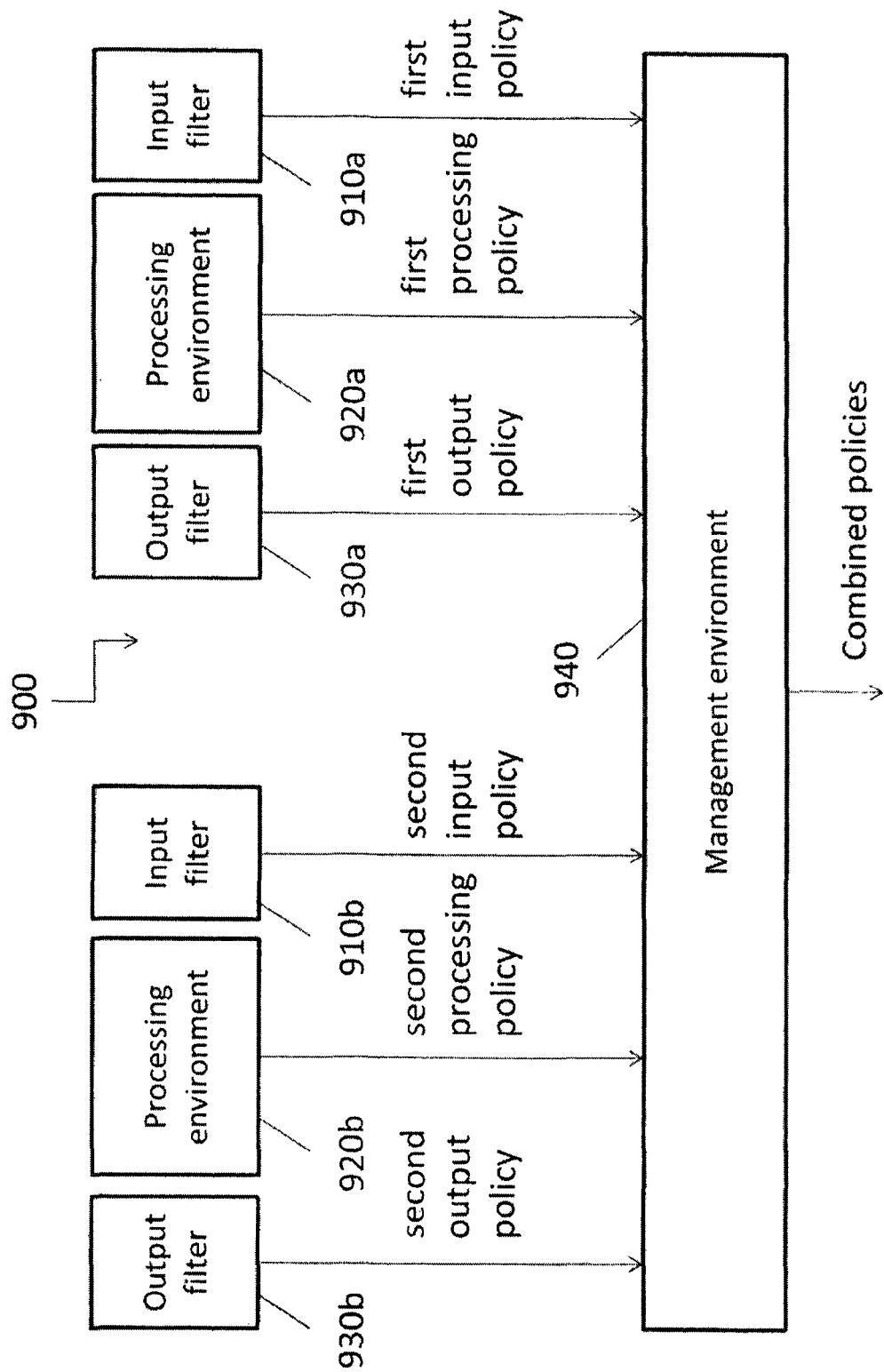
Figure 10:
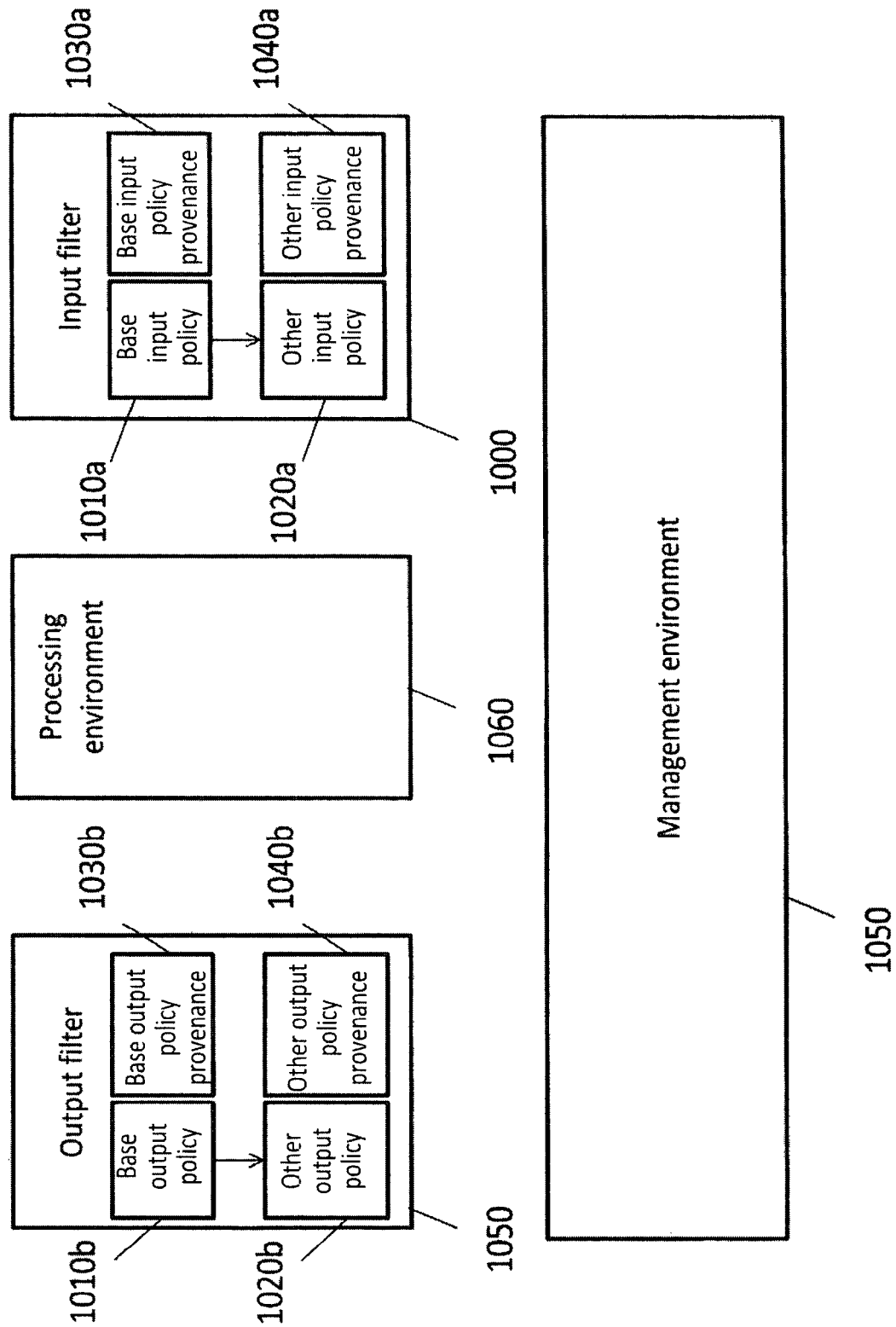

FIG. 9 schematically shows an arrangement of combining policies together;

FIG. 10 shows an embodiment in which policies have provenance; and

Figure 11:
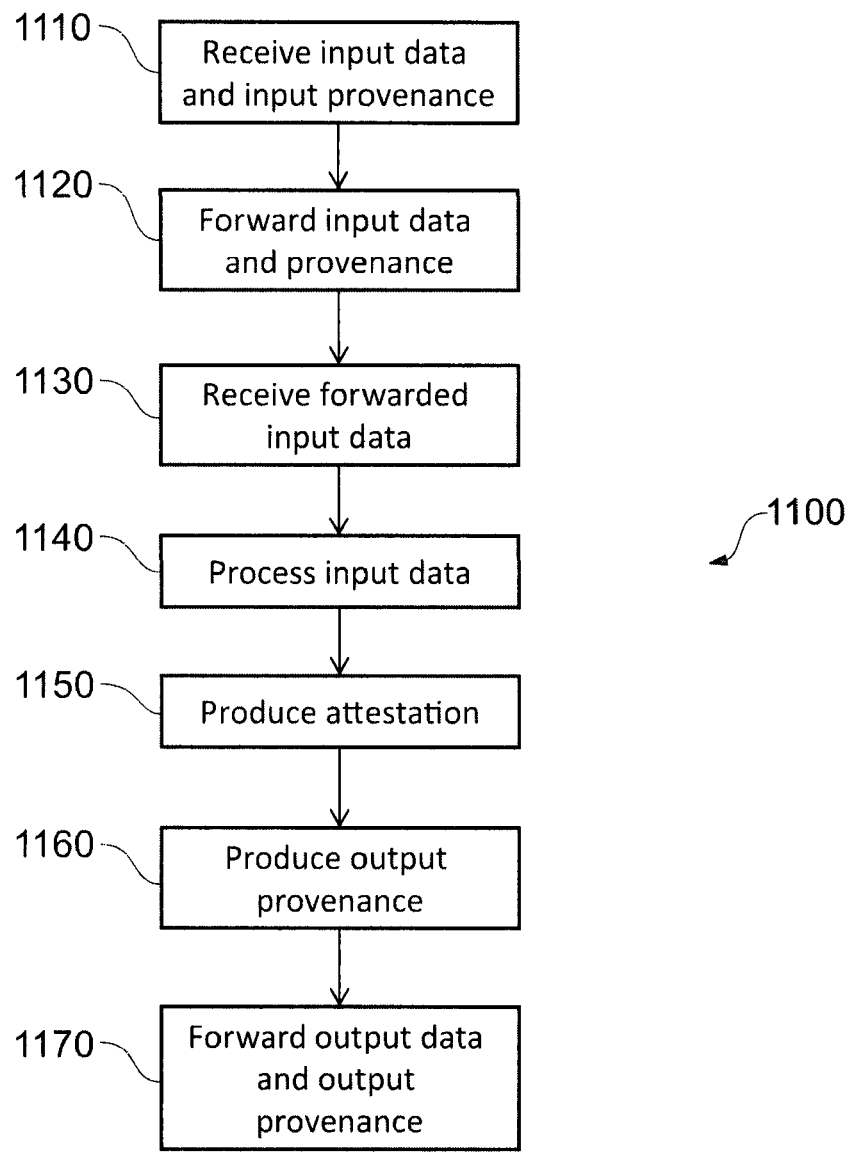

FIG. 11 illustrates a flow chart that shows an example of data processing in accordance with some embodiments.

In accordance with one example configuration there is provided a data processing apparatus comprising: an input policy filter to receive input data and an input provenance that relates to the input data, and to forward some or all of the input data and the input provenance according to at least one input policy; a processing environment to receive the input data forwarded by the input policy filter and to process the input data to generate output data; a management environment to produce an attestation of the processing environment and to produce an output provenance based on the input provenance and the attestation; and an output policy filter to receive the output data and the output provenance and to forward the output data and the output provenance according to at least one output policy.

Data is received by the input policy filter, together with provenance data relating to that input data. The input data (and the associated input provenance data) could be received from another data processing apparatus or could be received from another module (software or hardware) within the same data processing apparatus. In either case, the input policy filter of the data processing apparatus consults an input policy to determine how the input data and/or input provenance information should be forwarded. Note that the input policy could dictate circumstances in which all, some, or none of the data and/or provenance information is forwarded and under what circumstances any such forwarding takes place. The processing environment receives any input data that has been forwarded to it by the input policy filter. The processing environment operates under the supervision of the management environment in order to produce output data. The processing environment could, for instance, take the form of a virtual machine under the supervision of a hypervisor (or even an application running under the supervision of the operating system on a hypervisor). Regardless, the processing environment is unable to affect the management environment and is not able to leak information—it is supervised by the management environment, and communicates via the input policy filter and output policy filter. The management environment produces an attestation as to the processing environment. The attestation is a verification or assertion that the processing was performed by the processing environment and that the processing that was performed is what was expected to be performed. This attestation can then be used together with the input provenance in order to produce an output provenance. Thus, the output data is attested for by the output provenance. Both the output data and the output provenance are provided to the output policy filter, which forwards these based on an output policy. As with the input policy, the output policy may dictate that some, none, or all of the data and/or provenance information is forwarded and under what circumstances. In this way, control can be kept over the data, particularly over the way it is processed and used.

In accordance with some embodiments, the at least one input policy comprises at least one input provenance condition; and the input data and the input provenance are forwarded according to the at least one input provenance condition. By including a provenance condition, it is possible to control the input data so that only input data that has been processed in a particular way can continue to be processed by the processing environment.

In some embodiments, the input provenance condition is applied to a subset of inputs to the input policy filter; and in response to the input provenance condition being missed, an error is triggered. There are a number of ways in which the subset of inputs (each comprising input data and an input provenance) can be selected. In some embodiments, the subset is selected randomly in that each input has a 1-in-N chance of being selected for testing. In other embodiments, every M'th input is checked for the presence of the condition. In any case, when the condition is missed, an error can be triggered. In this way, it is possible to effectively "spot check" each input. This may be appropriate for use in systems where checking the input provenance is time consuming or computationally expensive. Rather than checking every single input as to whether the input provenance is appropriate, such embodiments make it possible to only perform checks in a fraction of inputs. There are a number of different examples as to an appropriate condition. One example could be that the input provenance does not have the requisite chain of processing that might be expected. For instance, if the processing environment expects data that represents a heart rate of a user, then the input provenance may be considered to be invalid if no evidence of processing by a heart rate monitor can be found in the input provenance. Similarly, in a secure system in which reliability is necessary, the condition may be missed if the input provenance indicates that the heart rate has not come from one of a variety of selected, trusted heart rate monitors whose outputs are considered to be sufficiently reliable for processing to be performed. This makes it possible for a processing module to refuse to operate and/or take responsibility for data that is considered to be potentially unreliable.

In some embodiments, the input policy filter is adapted to inhibit the input provenance from being passed to the processing environment, and is adapted to forward the input provenance to the management environment. In such embodiments, it is considered to be undesirable for the input provenance to be passed to the processing environment. This prevents the processing environment from having anything to do with the input provenance and in particular prevents the input provenance from being probed, which may take place as a precursor to modifying or forging the provenance. This act can also be used in order to provide more robust security and privacy. If particular information regarding the provenance is desired to be accessed by a processing environment further down the chain in the overall system, then this information can be provided as part of the input data itself. By providing data as part of the input provenance, it may be assumed that such data is considered to be privileged and therefore not for consumption by the processing environment itself but rather to be limited by, for instance, the management environment.

In some embodiments, the at least one input policy restricts forwarding of the input data based on an identity of a source of the input data, and the at least one output policy restricts forwarding of the output data based on an identity of a target of the output data. In these embodiments, the input policy and/or output policy inhibits data from flowing from or to unknown or untrusted environments. In this way, data can be restricted to being provided by a specific other processing environment and can be restricted to being provided to a specific further processing environment. For instance, in the case of heartrate data, the output policy may restrict forwarding of heart rate data to anyone other than a medical professional. Similarly, the input policy may restrict the provision of data from anything other than a health service recognised heart rate monitor.

In some embodiments, the at least one input policy comprises a plurality of input policies the input policy filter applies one of the plurality of input policies; and the one of the plurality of input policies is selected in dependence on a data source of the input data or a type of the input data. In these embodiments, a number of different input policies are provided. The input policy that is applied by the input policy filter depends on a data source of the input data. In this way, it is possible of provide different restrictions depending on the input provider. This could be used to allow different processes to be performed on inputs depending on the source of the input data. For instance, a heartrate monitor that is health service registered could be used for a process that determines if the user has an abnormal or unhealthy heart rate, while a heartrate monitor that has not been registered with a health service may be considered to be inappropriate (liable to miss danger signs or liable to see danger where there is none). However, heartrate monitors that are both registered and unregistered by that health service may be used in order to provide data to a process that it used for fitness monitoring, where reliability or accuracy may be a lower concern.

In some embodiments, the at least one output policy comprises a plurality of output policies; the output policy filter applies one of the plurality of output policies; and the one of the plurality of output policies is selected in dependence on a target of the output data or a type of the output data. The output policy may comprise a plurality of output policies and one of those output policies may be applied in dependence on a target of the output data. In this way, data can be restricted in different ways depending on the target of the output data. For instance, if the target is a medical professional, then heartrate data for the last 24 hours, in raw form, could be provided. In comparison, if the target is a fitness application, then it may only be appropriate to provide the latest average heartrate value every 60 seconds.

In some embodiments, the input data comprises data received via a plurality of data sources and; the input provenance comprises provenance information relating to each of the plurality of data sources. By providing provenance information that relates to each of the plurality of data sources through which the input data has been computed, it is possible to produce a "chain" of provenance from the origin of the initial data through to the current processing environment, with each point in the chain representing processing that was performed by different processing environment on the data that was received. This can be used in order to provide an "audit trail" of the processing that has been performed. This could make it possible for a processing environment to only operate on data that is considered to be trusted, reliable, and has had any necessary processing steps performed on it. One way in which this could be used is to ensure that anomalies or background noise are removed from data before the data is processed. In such a case in may not necessarily be required that this was the immediately previous step to a particular processing environment operating on the data, but it may be necessary that such a step has been performed somewhere in the chain in order that such unreliable data has been filtered.

In some embodiments, the attestation of the processing environment comprises a hash of at least part of the processing environment. A hash can be considered to be a mathematical operation that translates an input in an input domain to an output in an output domain where the output domain is smaller than the input domain. In this way, an input can be represented by its hash value. The hash value could be secure such that it is mathematically intractable to either find two inputs that produce the same hash value or to provide an input given its corresponding output. Consequently, by providing a hash of the processing environment that produces the output data from the input data, it may not be possible to immediately determine from the hash what processing is performed, but it may be possible to verify that the expected processing environment was used in order to produce the output data. If even a small modification is made to the processing environment, then this would result in a change to the hash value that could be detected. Indeed, hash functions often have the property that a small change to the input value creates a large change in the hash value. This can therefore provide a protection against the processing environment being subtly or slightly modified (potentially as a result of being hacked).

In some embodiments, the attestation of the processing environment comprises a hash of the output data. By providing a hash of the output data itself as the attestation of the processing environment, it is possible to verify or confirm that the output data is the result of the processing environment performing processing on the input data. In some of these embodiments, the attestation may also include the output data so that the hash can be confirmed or could include the input data so that the processing performed by the processing environment can be performed again, in order to obtain the output data and thereby confirm that the hash value is correct.

In some embodiments, the input provenance is cryptographically signed; and the management environment causes the attestation of the processing environment to be cryptographically signed. Cryptographic signatures make it possible to authenticate the origin of some data that can been cryptographically signed. As a consequence of the input provenance being signed, it is possible to rely on the stated origin of that data being accurate. Similarly, as a consequence of the management environment causing the attestation of the processing environment to be cryptographically signed, it is possible for other environments to be able to rely on the processing environment by virtue of its origin. Note that the attestation itself may not be directly signed. In particular, the attestation of the processing environment could be cryptographically signed by virtue of the output provenance (produced by using the attestation) being signed. A cryptographic signature process could involve one or more certifying authorities. Such authorities may be third party entities that do not take responsibility for the processing environment itself, but instead serve as to verify the authenticity of the entity that signs the processing environment. For instance, rather than explicitly keeping track of each heart rate monitor that a health service has registered, it may instead be acceptable to instead trust any heart rate monitor that has been cryptographically signed by an entity that is certified by a health service. In this way, the health service would certify one or more third parties to sign processing environments that produce heart rate data. Those third parties would be trusted by the health service to produce trusted data. In this manner, a chain of certification can be provided. Furthermore, one could consider a government authority signing a certificate of a national health service in order to verify that the national health service was recognised by a government. Such a chain can continue almost without limit. A certifying authority may also have the ability to revoke certification if it subsequently turns out that the trust provided by that certifying authority was misplaced. For instance, if a hardware manufacturer that was certified by a national health service was found to be producing poor quality heart rate monitors, then the national health service could revoke its certification of that hardware manufacturer by publicly revoking the government-issued certificate validating that manufacturer's product. These techniques will be known to the skilled person.

In some embodiments, the processing environment is signed with a cryptographic signature; and the management environment is adapted to check validity of the cryptographic signature. By signing a processing environment (for instance, the software that runs within or that makes up the environment), it is possible to provide a degree of reliability that a processing environment is authenticated and/or manufactured by a particular entity. In some cases, the cryptographic signature may make use of a certificate chain in order to identify the provider of the processing node. The validity of the cryptographic signature could be checked by confirming that the provider (e.g. the signer of the processing environment) is certified to provide a processing environment that performs the specified function.

In some embodiments, the at least one input policy comprises at least one of a required input data type, a maximum input data quantity, a maximum input data rate, and a maximum input data latency. The policy could therefore restrict the output data in a number of different ways including the type of the data (e.g. float, integer, double, char, boolean), a maximum input data quantity (e.g. 40 bytes), and a maximum input data rate (3 times per day). This can be used in order to help guarantee that input data is of the expected format, and quality. Other Quality of Service metrics that can be the subject of the filtering will be known to the skilled person. Note that type checking can be achieved using regular expressions or language parsers. A type need not be confined to regular types and could be custom-defined types that are recognised throughout the system. For instance, one might define a type "HeartRate" that represents a number of beats per minute and is an unsigned 8-bit integer (thereby representing integer values of 0-255). A policy could therefore reject the type "unsigned integer" but allow the custom type "HeartRate" as produced by a heartrate monitor. Latency can be determined by providing a time stamp during the attestation process performed by the management node.

In some embodiments, the at least one output policy comprises at least one of a required output data type, a maximum output data quantity, a maximum output data rate, and a maximum output data latency. In a similar manner to that of the input policy, the output policy could also restrict the output data based on a required output data type, a maximum output data quantity and a maximum output data rate. For example, data may be restricted from being output more than 12 times per day, with at least 55 minutes apart between each output. By restricting output in this way, it is possible to conserve bandwidth. Again, other Quality of Service metrics that can be the subject of the filtering will be known to the skilled person. Note that type checking can be achieved using regular expressions or language parsers. As above, a type need not be confined to regular types and could be custom-defined types that are recognised throughout the system. Latency can be determined by providing a time stamp during the attestation process performed by the management node.

In some embodiments, the at least one output policy comprises a requirement that a type of the output data matches a type of the input data.

In some embodiments, the output filter is adapted to perform a conversion from a type of the output data to a type of the input data in response to the type of the output data being different to the type of the input data. For instance, this could involve the conversion of an integer 16 to a floating point number 16.0. Furthermore, this could occur via the aggregation or separation of data. For instance, if only an array of 16 integers can be output according to the output policy then the output filter could include a buffer to store a most recent other 15 integers that have been presented. When a $16^{th}$ integer is presented, this can be packaged with the other 15 most recent integers to form an array of 16 integers that can be output by the output filter. Similarly, if an array of 16 integers is received, but only single scalar integers are permitted then then output filter could buffer the received array of 16 integers and output these, over a period of time, as scalar integers. The skilled person will appreciate that in some embodiments, similar conversions could take place at the input filter.

There are a number of different ways in which the output provenance can be produced. However, in some embodiments, the management environment is adapted to produce the output provenance by concatenating the attestation with the input provenance. A concatenation of the attestation with the input provenance makes it possible to examine the output provenance and access the attestation of any particular processing environment in the chain. This can then be used to verify the attestation at one of more different stages. For instance, if the attestation takes the form of a hash of the executable code and its local data and configuration, then the attestation can be compared to a known value. Similarly if the attestation takes the form of a hash of the result of executing the code then if the input value for a given attestation is known (for instance, if this also forms part of the attestation) then this can be hashed in order to verify whether the hashes match (thereby indicating that the attestation is valid).

In other embodiments, the management environment is adapted to produce the output provenance by merging the attestation with the input provenance. A merging of the attestation with the input provenance means that it may not be possible to separate the attestation and the input provenance. Consequently, although the result may be considered to be fixed such that all previous steps of the chain could be relied upon, it may not be possible to access information relating to one specific part of that chain at a later time. However, by merging the attestation with the input provenance, the entire chain need not be stored and consequently the output provenance can be reduced in size without sacrificing the integrity of the chain itself.

In some other embodiments, in response to the input provenance meeting a condition, the management environment is adapted to produce the output provenance by outputting the attestation.

There are a number of examples of what such a condition could be. However, in some embodiments, the condition comprises a requirement that the input provenance is verified. In particular, if the input provenance is verified then it may be considered to be acceptable to lose the input provenance and instead provide only the attestation, particularly if the data processing apparatus is trusted. In such embodiments, the input provenance that is lost could be stored locally at the data processing apparatus for later retrieval if necessary. By not including the input provenance in the output provenance, it is possible to reduce the size of the output provenance as compared to situations where the input provenance is included.

In some embodiments, the processing environment is adapted to process the input data or the output data to generate further output data; and the output policy is adapted to permit forwarding of the further output data in dependence on the output data. In some cases, the input data itself may be processed in multiple ways. Consequently, the input data may be processed in a first way as to produce output data and a second way in order to produce further output data. Where this occurs, there may be some embodiments in which the output policy permits the output data to be forwarded as well as the further output data to be forwarded depending on the output data itself.

For example, in some embodiments, the output policy is adapted to permit forwarding of the further output data in dependence on the output data having a given characteristic. Consequently, when the data itself has a particular given characteristic, the further output data may be "unlocked" such that it can be forwarded (subject to the conditions of the output policy). For instance, in the case of a heart rate sensor, if the output data indicates that the user is at risk of having a heart attack, then further output data providing more specific information that would otherwise be undesirable to free the output, may be freely provided in order to enable the opportunity for the user to be provided with assistance.

In some embodiments, the management environment is provided by a hypervisor; and the processing environment is a virtual machine that is managed by the hypervisor. There are a number of different ways in which the management environment and the processing environment can be embodied. However, in some cases, the management environment is provided by a hypervisor. The hypervisor may manage a number of different virtual machines, one of which could be the processing environment. It will be appreciated that in such embodiments, a number of different processing environments could be provided each being isolated by virtue of being a different machine under the supervision of the same hypervisor. In this way, the same management environment could manage a number of different processing environments each of which is interlinked by input policies and output policies. The management environment itself could also be a virtual machine operating under the hypervisor. In either case, each processing environment is isolated by virtue of being a virtual machine and is isolated from the management environment again by virtue of being a virtual machine operating under the hypervisor.

In some embodiments, the management environment is adapted to control a behaviour of the processing environment to operate according to at least one processing policy.

In some embodiments, the at least one processing policy comprises a state reset condition; and in response to the state reset condition being met, the management environment causes a processing state of the processing environment to be reset. By resetting the state of the processing environment, it becomes difficult for the processing environment to carry data over from one input to another. This therefore reduces the chances of the processing environment leaking data.

In some embodiments, the at least one processing policy comprises a logging condition; and in response to the logging condition being met, the management environment causes a processing state to perform logging. The logging condition could, for instance, be that every X-in-Y data inputs are logged, or could indicate a random probability with which a given input is logged. The condition could also indicate an extent to which logging occurs (e.g. a logging level). In some embodiments, the logged data is encrypted locally and, in response to a further condition, transferred to a data store.

In some embodiments, the at least one processing policy comprises one or more error handling rules; and in response to an error condition occurring in the processing environment, the management environment causes the error condition to be handled according to the one or more error handling rules. The error could, for instance, be an attempted policy violation (e.g. the input provenance being invalid, or the input filter refusing the input data due to its type). The one or more data handling rules could indicate how error handling occurs' on an error-by-error cases. For instance, certain errors could be notified in one way while other errors could be notified in another way. In some embodiments, an error handling routine is provided so that when any error occurs, it is passed to the error handling routine that determines how notification should occur based on the error type and on other circumstances.

In some embodiments, an attestation is provided in respect of at least one of the at least one input policy and the at least one output policy. In this way, a set of policies could be enforced by, for instance, a national health service, who may provide a set of policies on the type of data that should be used for heart rate monitors. These might, for example, require a particular resolution and/or quality of data.

In some embodiments, at least one of the at least one input policy and at least one output policy comprises a base policy and an other policy; and the other policy is at least as restrictive as the base policy. This could be used in order to form, for instance, a "graph" (e.g. "tree") of policies. By providing an other policy that is more restrictive than a base policy, it is possible to not simply meet the obligations of a given policy (e.g. as could be required by a national health service) but also to exceed those obligations—e.g. by requiring heart rate data of an even higher resolution than is required according to a national heath service's standards.

Particular embodiments will now be described with reference to the figures.

Figure 1:
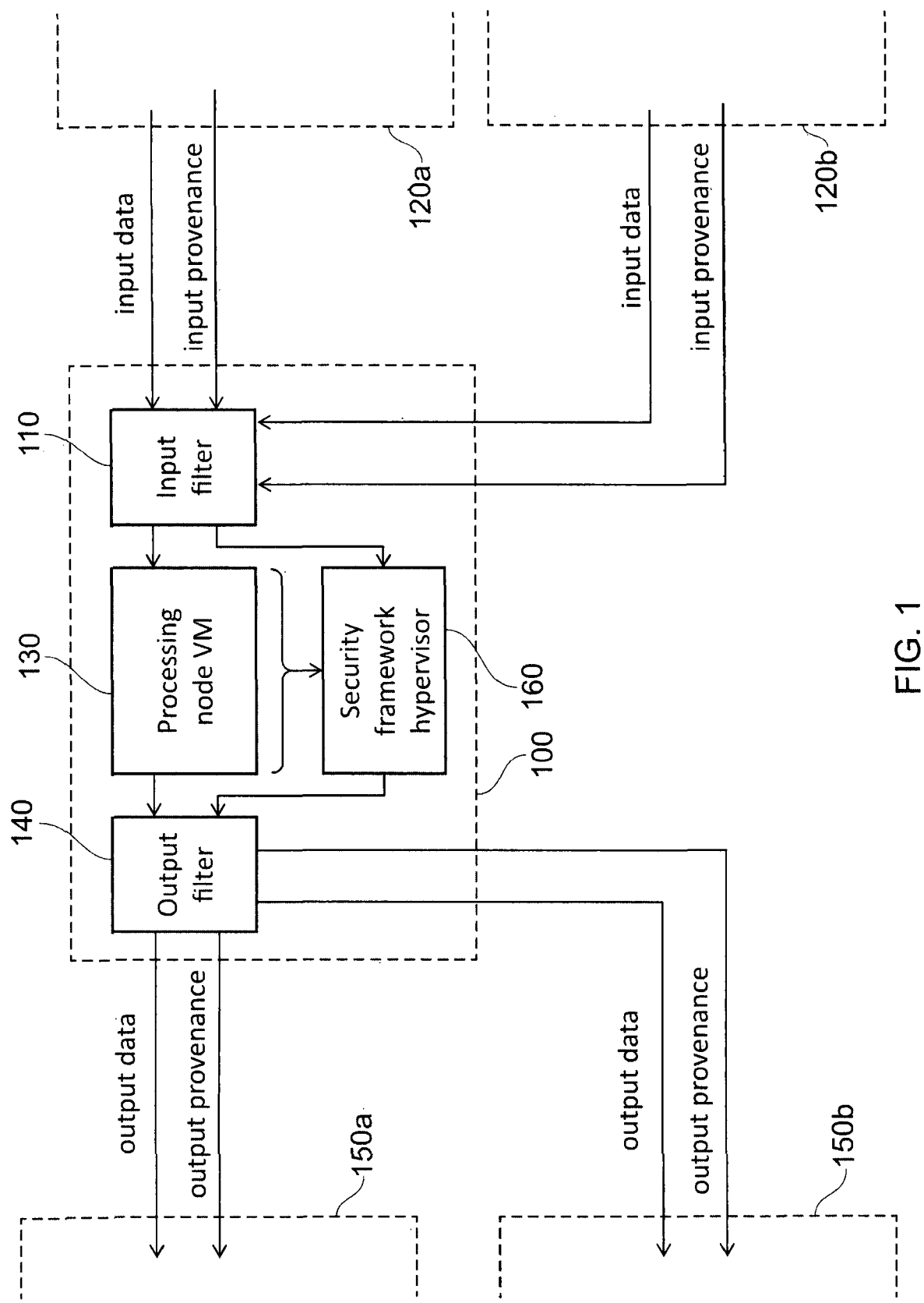
FIG. 1 illustrates an apparatus in accordance with some embodiments.

FIG. 1 illustrates an apparatus 100 in accordance with some embodiments. The apparatus 100 includes an input filter 110 (an example of an input policy filter) that receives input data and an input provenance from one of more input sources 120A, 120B. The input filter 110 acts according to one or more input policies and forwards the input data and the input provenance based on those input policies. In this example, the input data is forwarded to a processing node VM 130 (which is an example of a processing environment) and the input provenance is passed to a security framework hypervisor 160 (which is an example of a management environment). Note that this forwarding may take place on the basis of one or more requirements being met as dictation by the input policy or policies. The processing node VM 130 performs one or more processing operations on the input data in order to produce output data that is provided to an output filter 140. The security framework hypervisor performs an attestation on the processing node VM 130. This is used in combination with the input provenance in order to produce an output provenance that is provided to the output filter 140. The output filter 140 then provides the output data and the output provenance to one or more targets 150A, 150B. As with the input filter, the forwarding produced by the output filter 140 is based on one or more output policies. Consequently, the forwarding and the direction of the forwarding may be influenced by the output policies.

Figure 2:
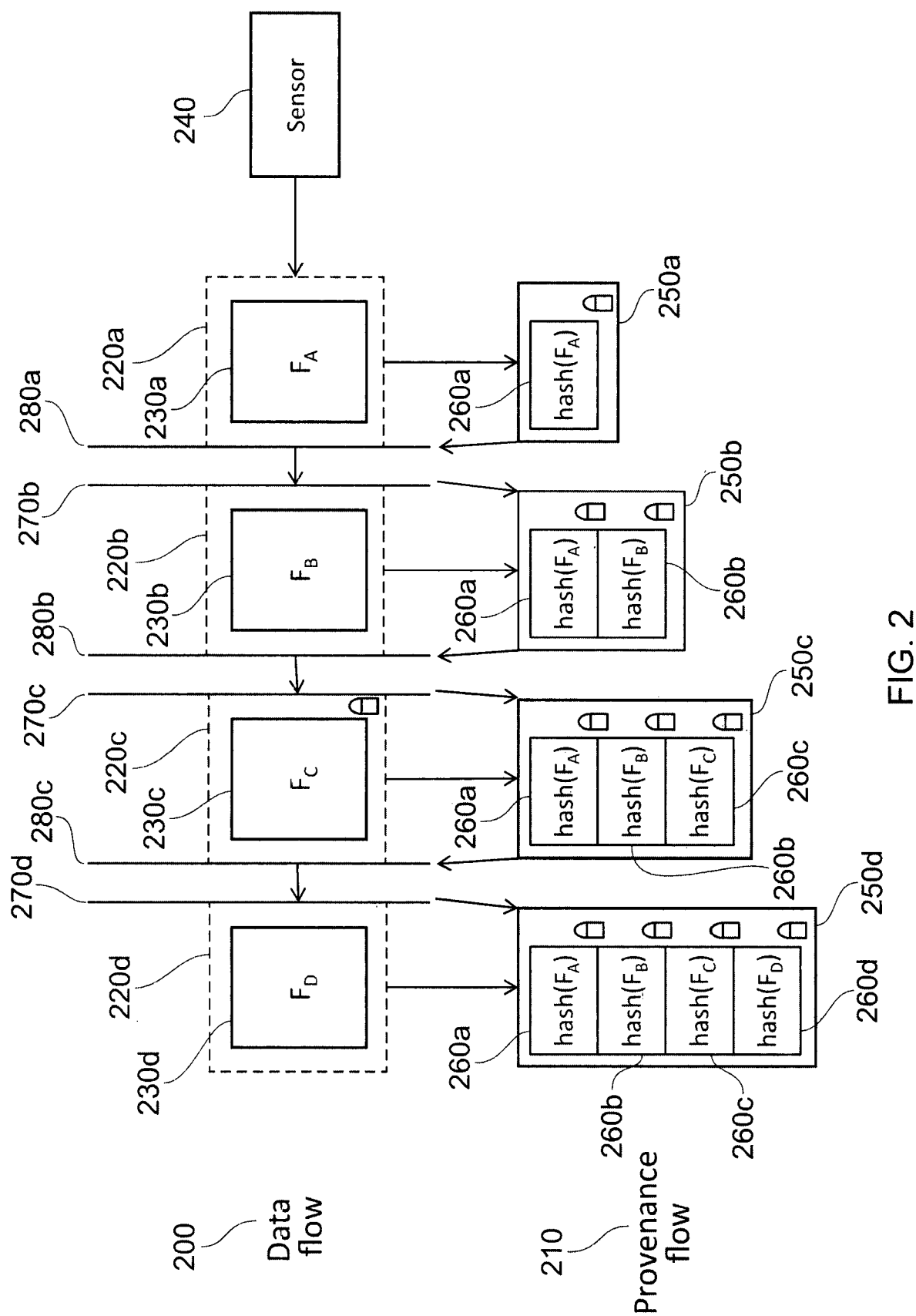
FIG. 2 illustrates an example in accordance with several embodiments of how the data flow and the provenance flow propagate.

FIG. 2 illustrates an example in accordance with several embodiments of how the data flow 200 and the provenance flow 210 propagate. In this example, sensor 240 is the ultimate source of data (e.g. heart rate data). This data is provided to a first node 220a, which may operate in a similar manner to the apparatus 100 illustrated with reference to FIG. 1. This node 220a contains a processing environment 230a that performs a first function $F_A$. The result of $F_A$ is then passed to a processing environment 230b of a second node 220b that performs a second processing operation $F_B$. The result of this operation is then passed to a third processing environment 230c, which is part of a third node 220c. This third processing environment 230c performs a third processing operation $F_C$. Finally, the result of this operation is passed to a fourth processing environment 230d, which is part of a fourth node 220d and performs a fourth processing operation $F_D$. Consequently, the data flow 200 is illustrated by the passing of the data through four processing environments 230a, 230B, 230c, 230d, each of which is provided in a separate node 220a, 220b, 220c, 220d. The inputs and outputs of each node 220 are filtered according to an input filter 270 implementing an input policy and an output filter 280 implementing an output policy, as was previously shown in FIG. 1. In this way, the data received by each node 220 can be restricted and, if necessary, forwarded according to the policies. Note that there is no output filter on the final node 220d. In this example, no data is output by the final node 220d and hence no output filter is required. Similarly, there is no input filter associated with the first node 220a since the first node 220a does not necessarily receive any input (the sensor may be considered to be a part of the first node 220a).

In addition to the data flow 200 described above, a provenance flow 210 occurs. Each node 220 contains a management environment 160, which is responsible for producing the attestation and provenance. In particular, the management environment 150 of the first node 220a performs an attestation 260a on the first processing environment 230a. Lacking any input provenance, this attestation 260a becomes the output provenance, which is passed to the second node 220b via the output filter 280a of the first node 220a and the input filter 270b of the second node 220b. The attestation is produced by performing a hash on the first processing environment 230a. The result of this hash is then cryptographically signed. In this example, the hash 260a is produced by performing the hash on the executable code that is executed by the first processing environment 230a. This becomes part of the provenance and can be checked at other nodes 220b, 220c, 220d to ensure that the hash corresponds with a predetermined hash of the first processing environment 230a. This would help to determine whether the processing environment itself 230a has been modified in order to perform a different function and also to confirm that the processing operation $F_A$ itself has been performed. The cryptographic signature can be used in order to determine that the node 220a itself performed the hash. This helps to prevent situation in which a different node attempts to masquerade as the first processing node 220a by surreptitiously performing a different processing operation to $F_A$ and providing the attestation as hash($F_A$). Since such a node would not have access to the relevant certificates/keys in order to perform cryptographic signing, the hash would remain unsigned. Consequently, other nodes would be able to determine that the hash value was not produced by the first processing node 220a. Such a technique can also be used in order to determine whether a particular node has been authorised or authenticated by an external agency. For instance, the first processing node 220a could be authorised by a central organisation such as a national health service. In any event, once the output provenance 250a has been generated, it is provided as part of the output to the second node 220b. This provenance is then extracted at the input filter 270b.

On being received by the input filter 270b of the second node 220b, the output provenance of the first node 220a (now the input provenance of the second node 220b) is forwarded to the management environment 160 of the second node 220. Here, the input provenance is combined with an attestation of the second processing environment 230b. In this example, the combination is achieved via a concatenation. Consequently, the output provenance of the second node 220b includes a cryptographically signed hash of the first processing environment 230a followed by a cryptographically signed hash of the second processing environment 230b. This is then output to the output filter 280b of the second node 220b. This output provenance is then output and is received by the input filter 270c of the third node 220c. This is again extracted and is combined with an attestation of the third processing environment 230c. The output provenance 250c of the third node 220c is therefore made up of three concatenated cryptographically signed hashes. Again, this is output by the output filter 280c of the third node 220c and is received by the input filter 270d of the fourth node 220d. Here, the attestation of the fourth processing environment 230d (again produced as a hash of the fourth processing environment 230d) is concatenated with the output provenance from the third node 220c and consequently the output provenance produced by the fourth node 220d is made up of four concatenated cryptographically signed hashes of each of the four processing environments 230a, 230B, 230c, 230d. Each of the hashes has been produced by a management environment 160 of the corresponding nodes 220a, 220b, 220c, 220d. Consequently, by analysis of the output provenance produced at the fourth node 220d it is possible to verify that each of the four processing operations $F_A$, $F_B$, $F_C$, $F_D$ has been performed. Furthermore, with each of the attestations having been cryptographically signed, it is possible to verify that each of the processing operations has been performed by an authorised device.

Figure 3A:
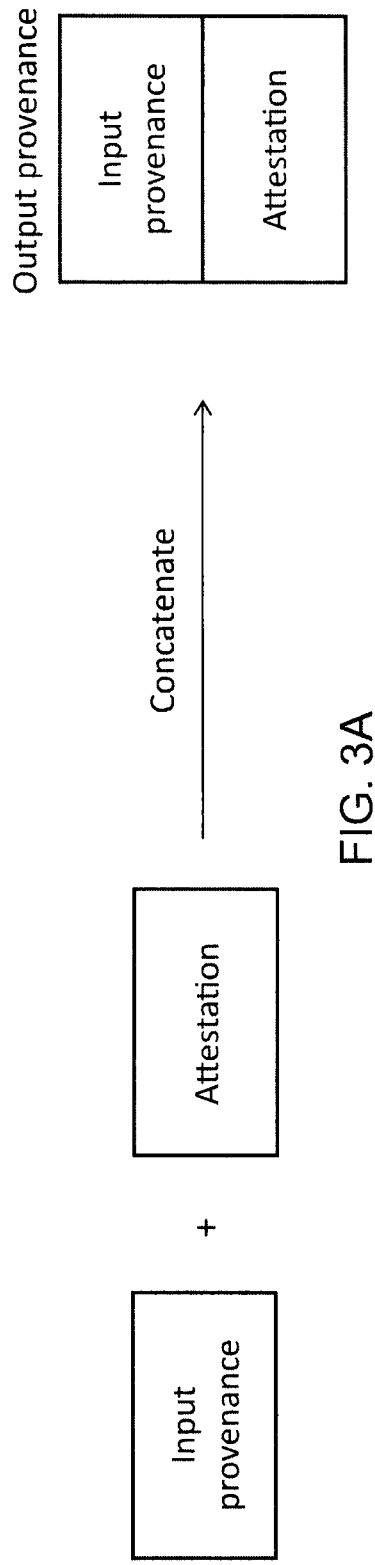
FIG. 3A illustrates how output provenance can be generated via concatenation.

In the example of FIG. 2, the output provenance was produced in each case by concatenating the input provenance with the attestation produced by the node. For instance, as shown in FIG. 3A, the input provenance plus the attestation of the local node is concatenated in order to produce an output provenance in which the input provenance is followed by the attestation. However, there are other ways in which the input provenance and the attestation can each be used in order to produce the output provenance.

Also in FIG. 2, it will be noted that the third processing environment 230c has been cryptographically signed. This enables the management environment to confirm that, for instance, an externally provided processing environment (e.g. software provided by a third party) is legitimate and makes it possible for the management environment to have confidence in the quality of processing performed by the processing environment 230c.

As an alternative, or in addition to the attestation being created by hashing the processing environment itself, it is possible for the attestation to include a hash of the output data produced by that processing environment (the input data and/or the output data could also be included). For instance, in the example of FIG. 2, the attestation of the first processing environment 230a could include a hash of the result of performing $F_A$ on the sensor data—i.e. hash($F_A$(input)). This could also include the input data itself, or the resulting output data itself $F_A$(input). Any of these could also be combined with (or provided instead of) a hash of the processing environment itself, e.g. hash($F_A$). In any event, the attestation is an indication that the processing environment performed $F_A$.

Figure 3B:
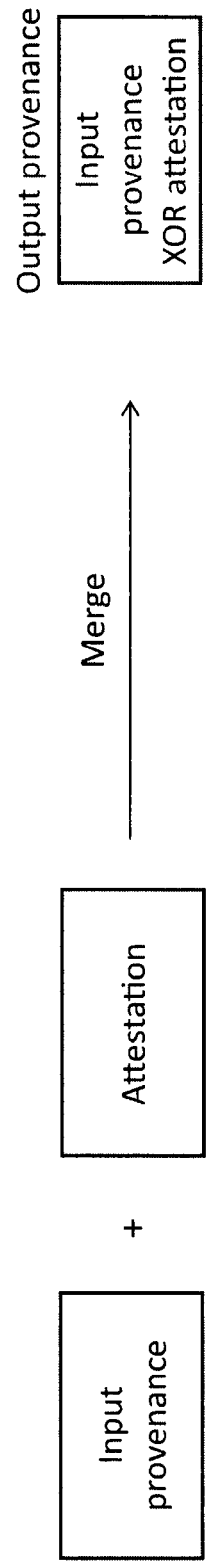
FIG. 3B illustrates how output provenance can be generated via merging.

In FIG. 3B, the input provenance and the attestation are merged together with order to produce an output provenance. For instance, the input provenance could be XORed together with the attestation in order to produce a combined piece of data. As a consequence of the two inputs being merged together, the output provenance may be expected to be no larger than the largest of the input provenance and the attestation. Consequently, the output provenance needs not grow at each stage. Furthermore, although such merging may lose the ability to individually confirm the attestation of a single processing environment, it may be possible to confirm the chain of processing provided that the same merging operation is used. For instance, taking the example of FIG. 2, although it may not be possible to individually determine that the processing environment $F_C$ is correct from the output provenance produced at the fourth node 220d, it generally remains possible to verify that the full chain of operations $F_A$, $F_B$, $F_C$, $F_D$ is correct and have been performed. Phrased differently, it may not be possible to determine from such an output provenance which of the four processing operations was not performed correctly, but it remains possible to determine that one or more of them was not performed correctly. In this example a XOR operation is used. This is because a XOR is both simple to implement in hardware and because the XOR operation maintains entropy unlike many other bouillon operations. Other appropriate forms of merging will be known to the skilled person. Note that in some embodiments the certificates might still be concatenated. This makes it possible for the authenticity to be confirmed at any stage.

Figure 3C:
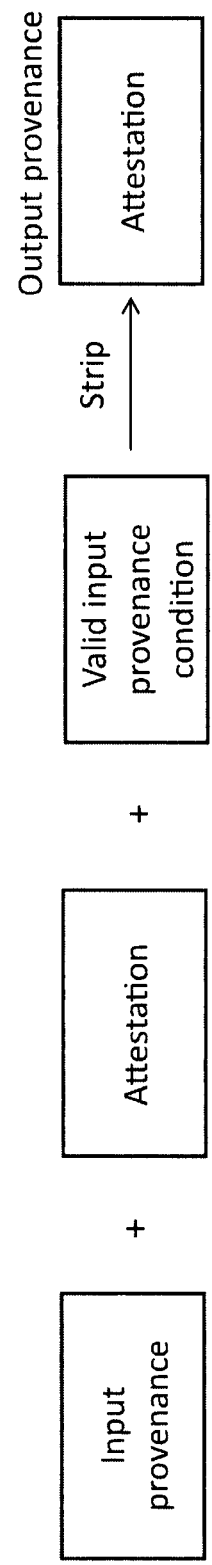
FIG. 3C illustrates how output provenance can be generated via removal.

FIG. 3C illustrates a third example in which the input provenance and the attestation are combined with the condition that the input provenance is considered to be valid. Here, having been verified, the input provenance is discarded such that the output provenance is the attestation itself. As with the example shown in FIG. 3B, this can result in an output provenance that does not necessarily grow at each stage. This is because the output provenance is approximately the same size as the attestation itself (differences may be due to overheads or headers for instance). However, this again removes the ability for later nodes to confirm the attestation of certain earlier nodes. In particular, in this example, although a node is able to confirm the provenance of its predecessor, a node cannot check the provenance of any earlier nodes. Indeed, each node is reliant on its predecessor in order to confirm that the provenance was valid. This requires the provenance to be checked as each stage. However, since it does not involve any concatenation or merging, the generation of the output provenance can be quicker than the example shown in reference to FIGS. 3B and 3A. Furthermore, less data must be transmitted between nodes than the examples shown in FIG. 3A. Again, in some embodiments, the certificates themselves could be kept rather than being discarded. In some embodiments, another condition (other than the input provenance being verified) may be used.

It will be appreciated that the selection of which of these examples is most appropriate will be dependent on the underlying application and also the implementation of the system. In a system in which each node is tightly controlled and tightly interconnected (e.g. executing on the same circuitry as different virtual machines), and particularly where each node has been produced by the same manufacturer, there may be little need for a particular node to verify the processing operation performed by far away nodes. Consequently, the example shown with reference to FIG. 3C may be appropriate. In other examples, such as where an audit trail is required (e.g. in a healthcare setting whereby verifiable data is necessary in case anything goes wrong), the example shown with reference to FIG. 3A may be more appropriate.

Figure 4:
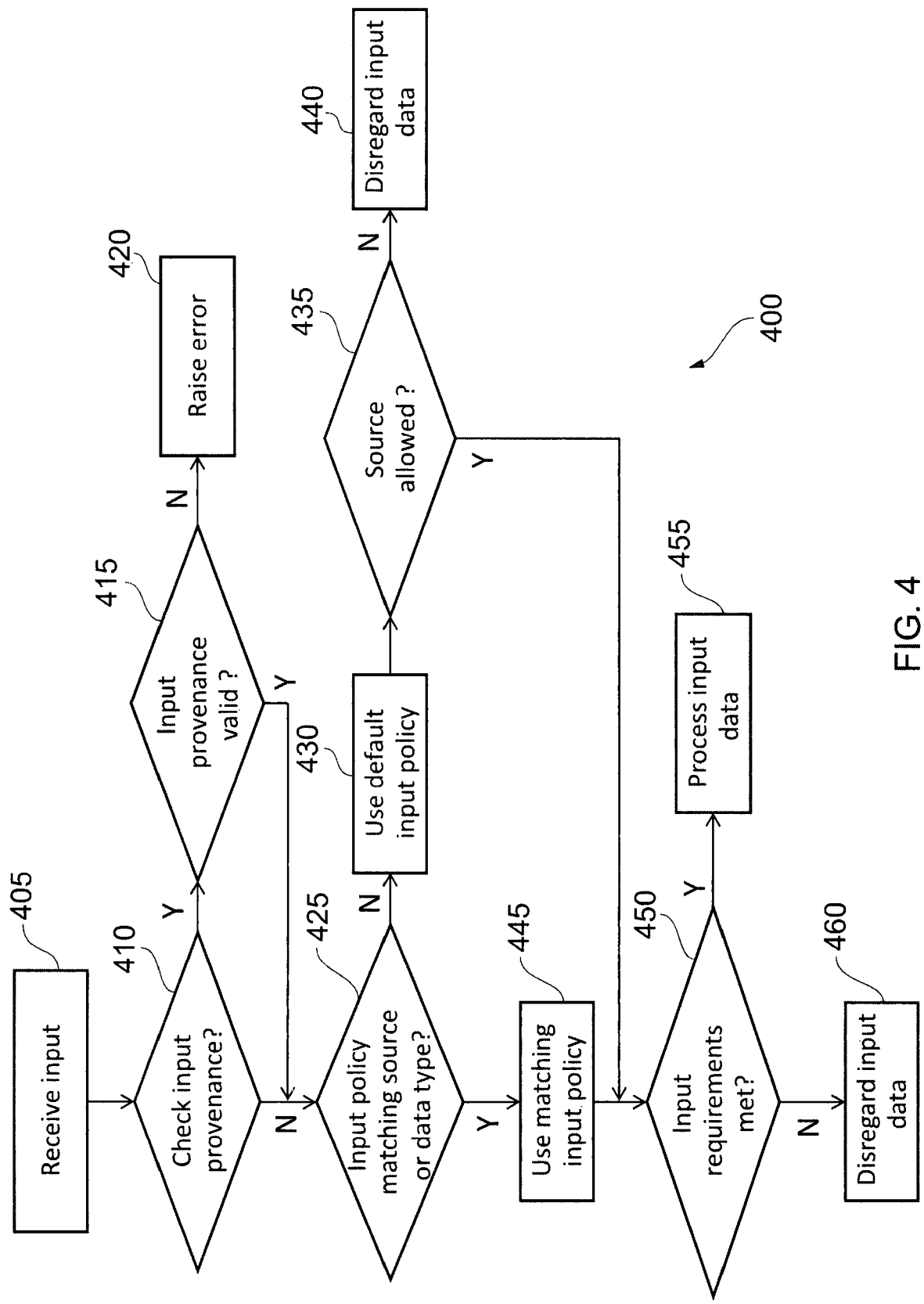
FIG. 4 illustrates a flow chart that shows an example of the processing operations performed at an input filter.

FIG. 4 illustrates a flow chart 400 that shows an example of the processing operations performed at an input filter 110 of a node 100. At a step 405, an input is received. At a step 410, it is determined whether the input provenance should be checked. In some embodiments, the input provenance of only a subset of the inputs is checked. For instance, inputs may be checked randomly or every X-in-N inputs may be checked. By performing such "spot checks" it is possible to maintain an element of security and reliability without necessitating the expenditure of processing power by checking the input provenance of every single input. Clearly, where reliability or security are considered to be of prime importance, such spot checking may not be used or a very large proportion of inputs may be spot checked. Similarly, where security or reliability are not required to such a large degree, or where the manufacturing environment is such that security or reliability concerned can be lessened, spot checks may become rarer. If, at step 410, it is determined whether the input provenance is to be checked, then at step 415 it is determined whether the input provenance is correct. If not, then at step 420, an error is raised. This could take the form of an exception, an alert to an operator, or could result in the system terminating altogether. If, however, at step 415 it is determined that the input provenance is valid, or if there is no need to check the input provenance at step 410, then at step 425 it is determined whether there is an input policy that matches the source or the data type of the input. If so, then at step 445, the policy that matches the source is selected and the process proceeds to step 450. If not, then a default input policy is used at step 430, and it is determined whether this source is permitted to provide data at step 435. If not, then at step 440 the input data is disregarded. The process could then return to step 405. If the source is allowed at step 435, then the process proceeds to step 450. Here it is determined, according to the input policy that has been selected whether the input requirements (e.g. Quality of Service metrics) are met according to the input policy that has been selected. Such requirements may relate to the input data type, quantity, quality, frequency, latency, and other Quality of Service metrics. If such requirements are met, then the input data is processed at step 455. Otherwise, the process proceeds to step 460 where the input data is disregarded. In either of these cases, the process may then return to step 405.

Note that in this embodiment, a verification failure results in the input data being disregarded. However, in some embodiments, particularly where one management environment manages a number of processing environments and where the input data provided to a previous processing environment can be obtained (e.g. if this is provided as part of the input provenance), then it may be possible to "rewind". For instance, if the data provided to a given input filter is invalid, then that data could be returned to the previous processing environment to be reprocessed. If the data that was originally provided to that previous processing environment is still available, then this can be reprocessed by the processing environment. Alternatively, if it is determined that the data provided to that previous processing environment was invalid and if a still further previous version of the data is available, then that still further previous version of the data could be provided back to a still further previous processing environment for processing, and so on.

Figure 5:
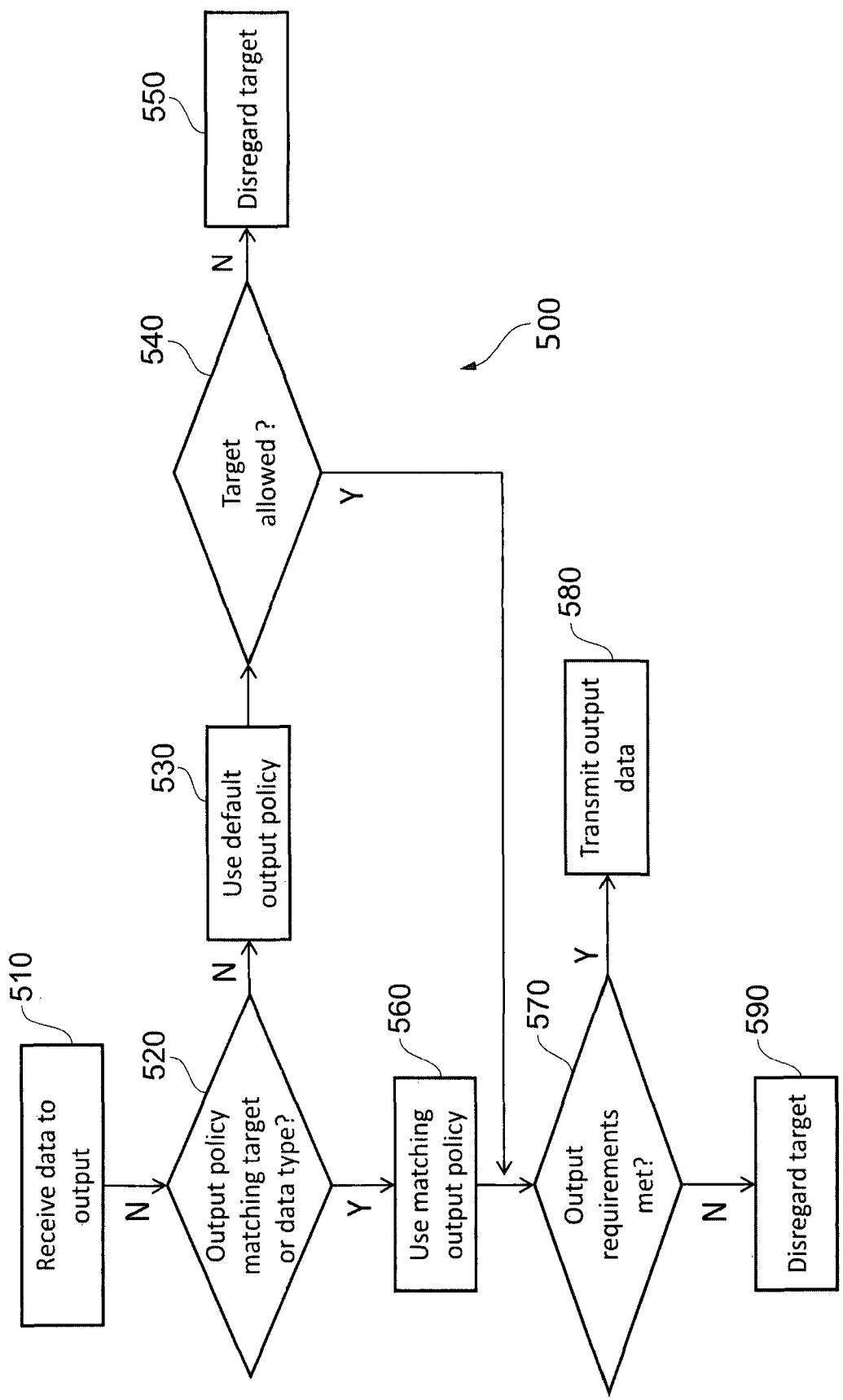
FIG. 5 illustrates a flow chart that shows an example of the processing operations performed at an output filter.

FIG. 5 illustrates a flow chart 500 that gives an example of the output filtering process that may be performed by the output filter 140 of a node 100. The process begins at step 510 where data to be output is received by the output filter. At step 520, it is determined whether there is an output policy that matches the target or the output data type. If so, then at step 560, that policy is selected to be used and the process proceeds to step 570. If not, then at step 530 the default output policy is used and the process proceeds to step 540. Here, it is determined whether the target is allowed. In other words, it is determined whether the output target is a target that is permitted to receive the output data. If not, then at step 550 the target is disregarded and no data is transmitted. The process may then proceed back to step 510. If the target is allowed, then the process moves to step 570 where it is determined whether the output requirements are met. As with the input filtering process shown with reference to FIG. 4, this is determined with reference to Quality of Service metrics (e.g. whether the data type/size/frequency/latency, etc is permissible according to the selected policy). If the requirements are met, then at step 580, the output data is transmitted. Otherwise, at step 590, the target is disregarded—or a warning message issued to a log file or log service. In either case, the process may then return to step 510. It will be appreciated that this process may be repeated for each target for which data is to be transmitted.

Figure 6:
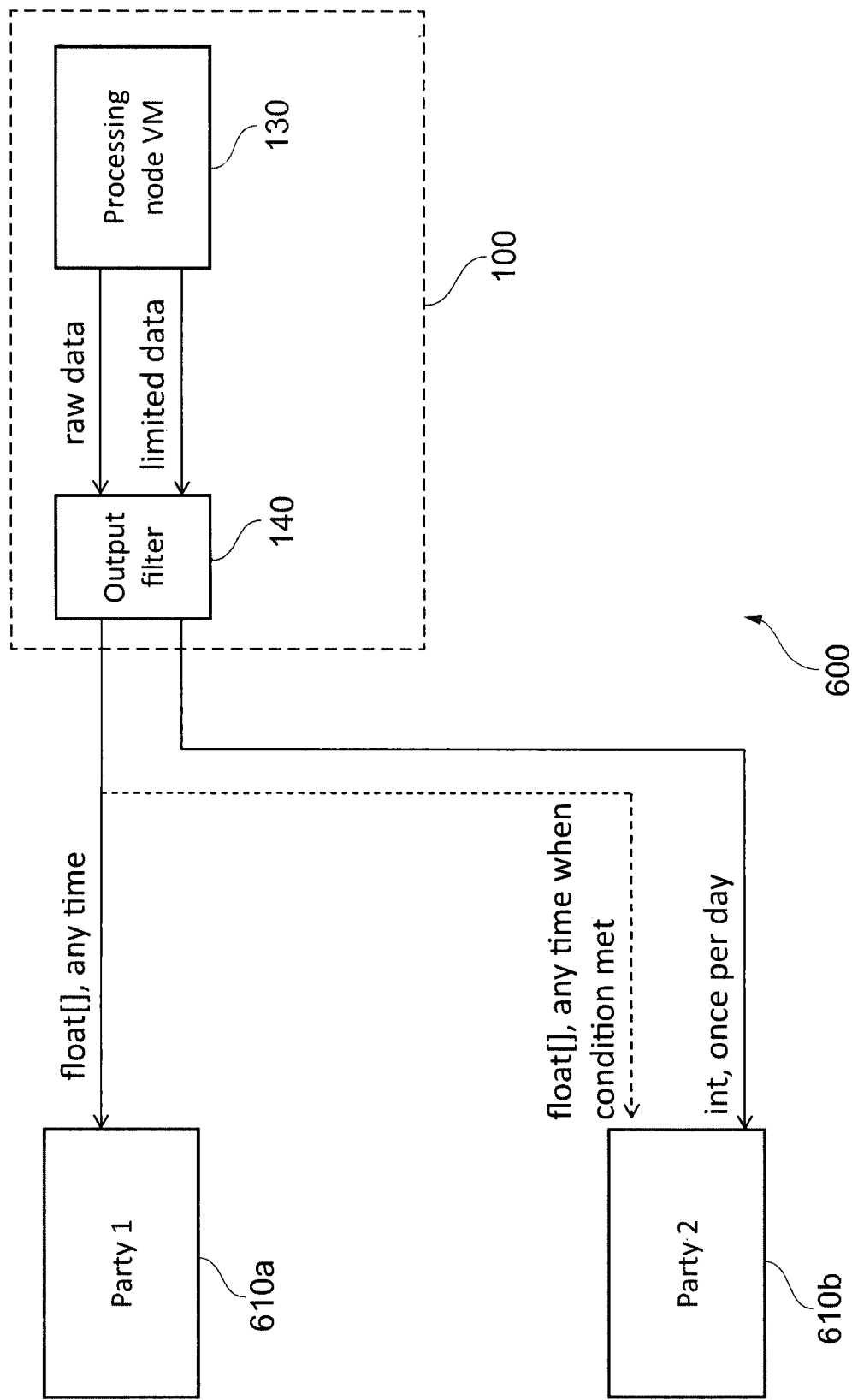
FIG. 6 illustrates an example in accordance with some embodiments in which data access can be "unlocked" by a particular target party.

FIG. 6 illustrates an example in accordance with some embodiments in which data access can be "unlocked" by a particular target party. In this example, the apparatus 100 is configured to output data via the output filter 140 to two different target parties 610a, 610b. Party 1 610a (e.g. a healthcare professional) is permitted to receive an array of floating point numbers at any time. This information may correspond with the raw data that has been received by a sensor such as a heart rate monitor for instance. Party 2 610b (e.g. an insurance company) is ordinarily only permitted to receive an integer once per day. This may correspond with the result of performing some processing on the data—for instance to provide an average heart rate over the day. Exceptionally however, when a particular condition is met, the second party 610b is also able to receive the array of floating point numbers. For instance, if the integer indicates that the user has a dangerously high average heart rate such that a heart attack is imminent or in progress, then the full range of raw data may be made available to the second party 610b. In some embodiments, the condition may be dependent on the environment such as the time or date. However, in other embodiments, the condition is dependent on the data that is otherwise output to the second party 610*b*. In this way, under these special or exceptional circumstances (conditions) it is possible for the more sensitive or privileged data to be unlocked or accessed by a party that does not ordinarily have access to it. This may be, for instance, in order to provide aid or help to the user where appropriate.

Figure 7:
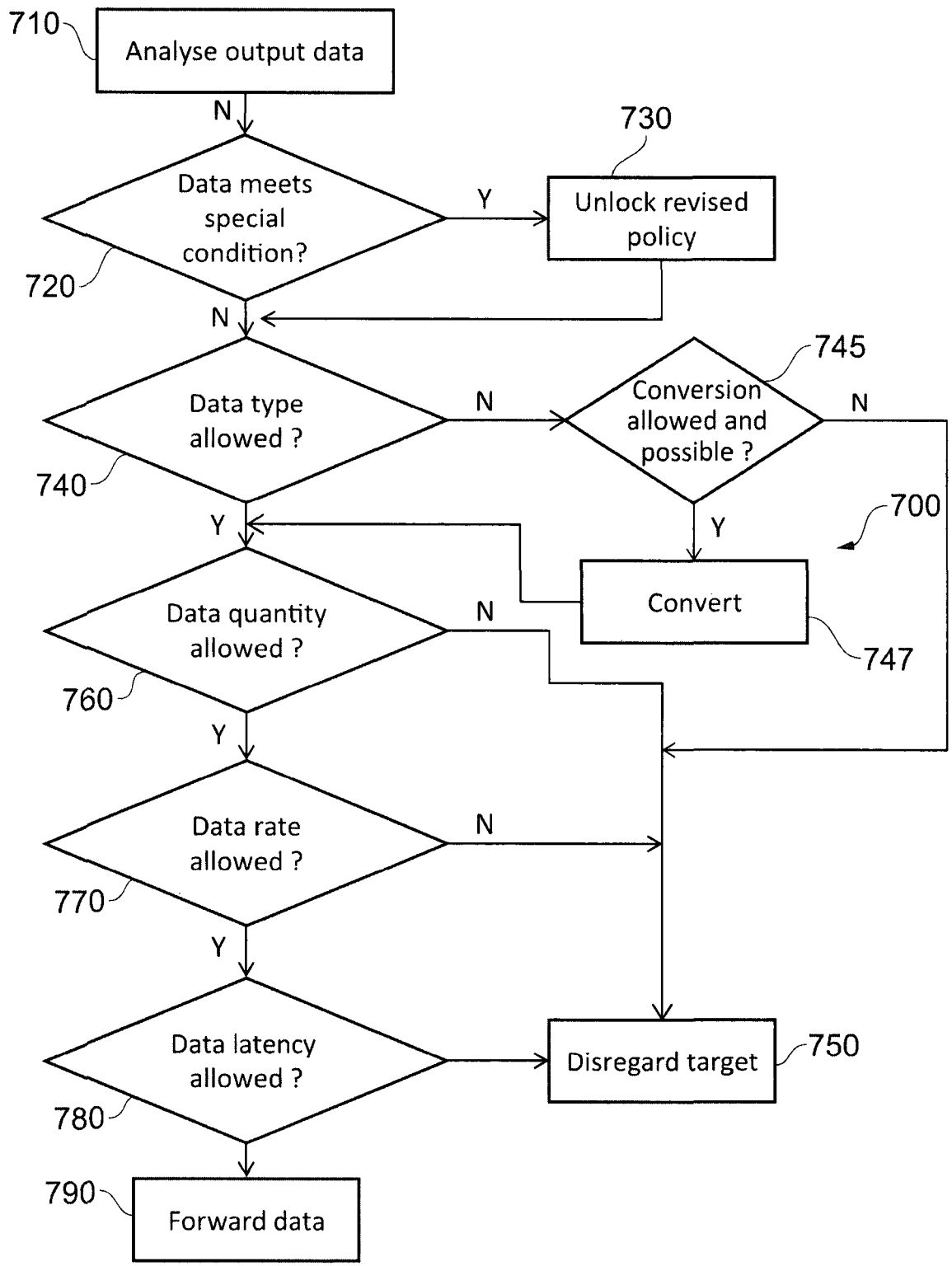
FIG. 7 illustrates the "unlocking" process in the form of a flow chart.

FIG. 7 illustrates this "unlocking" process in more detail in the form of a flow chart 700. At step 710, the output data is analysed in order to determine its type and to determine other factors that may be required according to the output policies. At step 720, it is determined whether any special conditions are met. If so, then at step 730, any policies that are "locked" with regards to those special conditions are unlocked thereby allowing those policies to be used. In any event, at step 740, having selected the most appropriate policy to use, it is determined whether the data type of the output data is allowed. In some embodiments, this could take place by determining whether a type of the input data matches a type of the output data. If not, then at step 745 it is determined whether a conversion from the current type of the output data to an allowed type of output data is permitted according to the output policy, and also whether such a conversion is possible. Rules for reformatting input or output can be classic type conversions such as the ones used in JavaScript, for example applied to the JSON data exchange format. If such conversion is possible, then at step 747, the conversion takes place and the process proceeds to step 760. Otherwise, the target is disregarded at step 750. If at step 740 the data type is allowed, then at step 760 it is determined whether the data quantity is allowed. If not, then again the process proceeds to step 750 where the target is disregarded. Otherwise, at step 770, it is determined whether the data rate is allowed. If not, then at step 750 the target is disregarded. However, if the data rate is allowed, then the data is forwarded at step 770. At step 780, it is determined whether the data latency is permitted. There are a number of ways in which this can be measured and compared. For instance, the management environment may (as part of the attestation) indicate the time taken to provide the output data after having received the input data and the output filter could disregard the data if there is too big a gap (e.g. if the processing has taken too long). This could also be achieved if multiple attestations are accessible in the provenance information by comparing the processing time from multiple attestations. In some embodiments, the latency could be measured from a time that it was initially generated, provided this data is maintained in the provenance data. In any event, if the data latency requirements are not met, then the target is disregarded at step 750. Otherwise, the process proceeds to step 790 where the data is forwarded. Note that steps 740, 760, 770, and 780 relate to Quality of Service requirements, which may be checked as part of the input policy in step 450 or the output policy at step 570 in FIGS. 4 and 5 respectively. In general, the selection of the most appropriate policy would involve selecting the most permissive policy that applies to the target (including any that have been unlocked at step 730). Where none of the policies are necessarily overall more permissive this process can be repeated in respect of each policy that applies to the output target or else the relevant policies can be compiled together, e.g. using a Satisfiability Solver (SAT Solver).

Figure 8:
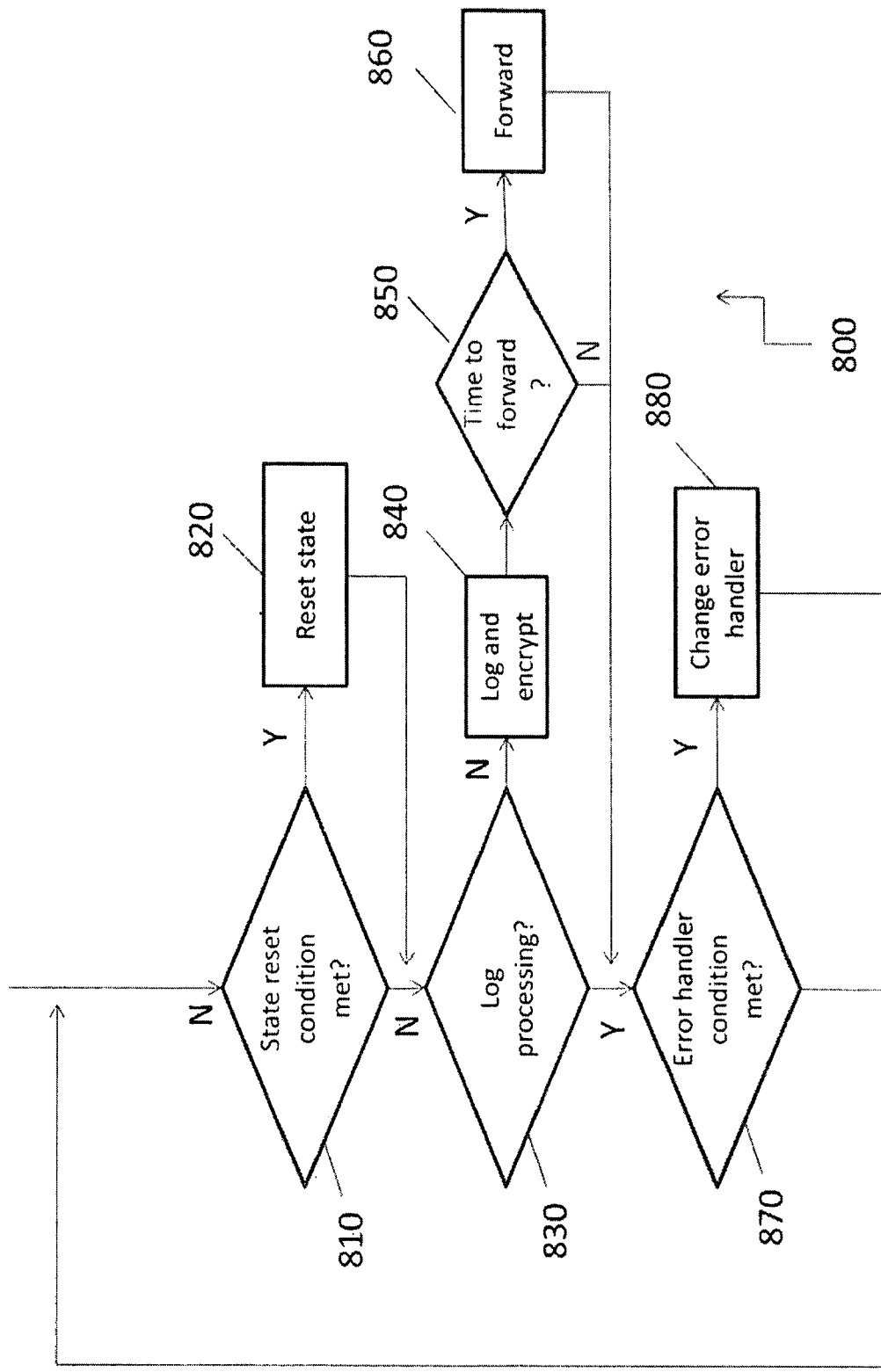
FIG. 8 illustrates a flow chart that shows an example of applying a processing policy.

FIG. 8 illustrates a flow chart 800 that shows an example of applying a processing policy. A processing policy can be applied by the management environment 160 in order to control behaviour of the processing environment 130, or the overall device. At a step 810, it is determined whether a state reset condition has been met. This is a condition under which an internal state of the processing node is to be erased. For instance, this could be after each item of input data has been processed, after every N items of input data have been processed, or at random (e.g. with a certain chance every time an item of input data is processed). If the condition is met, then at step 820, an internal state of the processing node is erased. This therefore prevents data from one input being carried out to another input. The state could be erased by actively erasing memory assigned to the processing node, or could be erased by assigning a new block of memory to the processing node, or by re-starting the processing node with newly allocated & reset memories, for instance. In any event, at a step 830, it is determined whether logging should be performed in respect of the processing node's operation. In other words, it is determined whether a logging condition is met. If so, then at step 840, logging is enabled and the contents of the log are encrypted by a public key (e.g. held by the management environment). At a step 850, it is determined whether the conditions are met such that the log can be forwarded to an external server. If so, then at step 860, the log is forwarded. In any event, the process then proceeds to step 870 where it is determined if conditions are met for a change in error handling routine to occur. If so, then at step 880, the error handler is changed. Consequently, errors that occur (such as attempted policy violations) may be handled in a different way such as being notified to a different entity (e.g. a supervising environment rather than a management environment). The process then returns to step 810. This entire process could be performed every period of time. In some embodiments the process is performed each time data is about to be processed by the processing environment 130.

FIG. 9 illustrates an arrangement 900 in which a first input filter 910*a* receives data and forwards it (as appropriate) to a first processing environment 920*a*. Having processed this, the data is then forwarded by a first output filter 930*a* (as appropriate) to a second input filter 910*b* for a second processing environment 920*b*. Here, the data received by the second input filter 910*b* is processed and passed to the second output filter 930*b* for further forwarding (again as appropriate). In this embodiment, each of the input policies, output policies, and (if used) processing policies are passed to the management environment 940. Here, the policies are combined and can be output as requested. This could allow a health care policy compliance inspector, for instance, to verify health care regulation compliance.

FIG. 10 illustrates an embodiment in which policies have provenance. For example, the input filter includes a base input policy 1010*a*, which is associated with a base input policy provenance 1030*a*. Here, the based input policy provenance 1010*a* verifies the base input policy 1010*a*. For instance, it may contain a cryptographic hash of the base input policy 1010*a*. The hash could also by cryptographically signed in order to verify that it comes from a particular source. Similarly, the output filter could include a base output policy 1010*b* with an accompanying base output policy provenance 1030*b*. The provenance of the policies can be verified by the management environment 1050. In the event of a verification error, the management environment 1050 could cause an error to be triggered. For instance, the entire device may refuse to operate, and/or an error might be flagged to an operator. In some embodiments, if the processing environment 1060 has an associated processing policy that defines an error handling routine, such a routine may be invoked in response to such an error. Such policies could be provided in the situation where a national health service dictates policies that are to be applied to particular systems. For example, a national health service may require that when performing heart rate monitoring in the case of a healthcare system, a certain resolution or quality of data is required. The provenance for such an input policy can then be provided to help verify that the policies being met are those enforced by the national health service.

Also in this example, an other input policy 1020a is shown, together with its associated provenance 1040a. In this case, the other input policy 1020a is designed to extend the base input policy 1010a. This permits the other input policy 1020a to tighten the requirements provided by the base input policy 1010a. Hence, the other input policy 1020a is not permitted to introduce any requirements that would not be met by the 1010a. This allows a processing environment to operate to even stricter requirements that they are necessarily obliged to by (in this example) the national health service. Again, such compliance can be confirmed by the management environment, e.g. by the use of a logic analyser (e.g. SAT solver). As before, if an other policy 1020a includes requirements that are not tightened requirements of a base policy 1010a then an error can be raised. Similarly to the other input policy 1020a, an other output policy 1020b can be provided that extends a base output policy 1010b. Similarly, in each case, the other policies 1020a, 1020b can each be accompanied by their own provenance information in order to help confirm the validity of those other policies. In this way, policies can be connected in a "graph" (e.g. tree) structure.

FIG. 11 illustrates a flow chart 1100 that shows an example of data processing in accordance with some embodiments. At step 1110, the input data is received together with the input provenance. At step 1120, the input data and the input provenance are forwarded in dependence on an input policy that is selected by the input filter. At step 1130, a processing environment receives the forwarded input data and at step 1140 the processing environment processes the input data. At step 1150, an attestation is produced. This may occur, for instance, via a management environment 160. At step 1160, this attestation is used together with the input provenance in order to produce the output provenance. Again, this may be performed by a management environment 160. Finally, at step 1170, the output filter receives the output data (which is produced as a consequence of processing the input data at step 1140) and the output provenance and these are forwarded to one or more targets based on one or more output policies.

Accordingly, via the above examples, it can be seen that it is possible to produce a system in which the receiving and the transmitting of data is accompanied by provenance information, which reflects the processing that has been performed on the input data so far. Furthermore, by continuing to provide attestations as to the processing that continues to be performed on the data, it is possible for later nodes in the chain of processing nodes to be confident as to the required quality of the data being operated on. Furthermore, it is possible to provide an audit trail for the purposes of security and reliability so that any faults or errors that occur can be traced back to the source of those problems.

In the present application, the words "configured to . . . " are used to mean that an element of an apparatus has a configuration able to carry out the defined operation. In this context, a "configuration" means an arrangement or manner of interconnection of hardware or software. For example, the apparatus may have dedicated hardware which provides the defined operation, or a processor or other processing device may be programmed to perform the function. "Configured to" does not imply that the apparatus element needs to be changed in any way in order to provide the defined operation.

Although illustrative embodiments of the invention have been described in detail herein with reference to the accompanying drawings, it is to be understood that the invention is not limited to those precise embodiments, and that various changes, additions and modifications can be effected therein by one skilled in the art without departing from the scope and spirit of the invention as defined by the appended claims. For example, various combinations of the features of the dependent claims could be made with the features of the independent claims without departing from the scope of the present invention.

The invention claimed is:

1. A data processing apparatus comprising:
an input policy filter configured to receive input data and an input provenance that relates to the input data, and to forward some or all of the input data and the input provenance according to at least one input policy;
a processing environment configured to receive the input data forwarded by the input policy filter and to process the input data to generate output data;
a management environment configured to produce an attestation of the processing environment and to produce an output provenance based on the input provenance and the attestation; and
an output policy filter configured to receive the output data and the output provenance and to forward the output data and the output provenance according to at least one output policy, wherein
the input provenance is cryptographically signed, and
the management environment causes the attestation of the processing environment to be cryptographically signed.

2. A data processing apparatus according to claim 1, wherein
the at least one input policy comprises at least one input provenance condition; and
the input data and the input provenance are forwarded according to the at least one input provenance condition.

3. A data processing apparatus according to claim 2, wherein
the input provenance condition is applied to a subset of inputs to the input policy filter; and
in response to the input provenance condition being missed, an error is triggered.

4. A data processing apparatus according to claim 1, wherein
the input policy filter is configured to inhibit the input provenance from being passed to the processing environment, and is configured to forward the input provenance to the management environment.

5. A data processing apparatus according to claim 1, wherein
at least one of:
the at least one input policy restricts forwarding of the input data based on an identity of a source of the input data, and
the at least one output policy restricts forwarding of the output data based on an identity of a target of the output data.

6. A data processing apparatus according to claim 1, wherein
the at least one input policy comprises a plurality of input policies;
the input policy filter applies one of the plurality of input policies; and
the one of the plurality of input policies is selected in dependence on a data source of the input data or a type of the input data.

7. A data processing apparatus according to claim 1, wherein
the at least one output policy comprises a plurality of output policies;
the output policy filter applies one of the plurality of output policies; and
the one of the plurality of output policies is selected in dependence on a target of the output data or a type of the output data.

8. A data processing apparatus according to claim 1, wherein
the input data comprises data received via a plurality of data sources and;
the input provenance comprises provenance information relating to each of the plurality of data sources.

9. A data processing apparatus according to claim 1, wherein
the attestation of the processing environment comprises a hash of at least part of the processing environment.

10. A data processing apparatus according to claim 1, wherein
the attestation of the processing environment comprises a hash of the output data.

11. A data processing apparatus according to claim 1, wherein
the processing environment is signed with a cryptographic signature; and
the management environment is configured to check validity of the cryptographic signature.

12. A data processing apparatus according to claim 1, wherein
the at least one input policy comprises at least one of a required input data type, a maximum input data quantity, a maximum input data rate, and a maximum input data latency.

13. A data processing apparatus according to claim 1, wherein
the at least one output policy comprises at least one of a required output data type, a maximum output data quantity, a maximum output data rate, and a maximum output data latency.

14. A data processing apparatus according to claim 1, wherein
the at least one output policy comprises a requirement that a type of the output data matches a type of the input data.

15. A data processing apparatus according to claim 1, wherein
the output filter is configured to perform a conversion from a type of the output data to a type of the input data in response to the type of the output data being different to the type of the input data.

16. A data processing apparatus according to claim 1, wherein
the management environment is configured to produce the output provenance by concatenating the attestation with the input provenance.

17. A data processing apparatus according to claim 1, wherein
the management environment is configured to produce the output provenance by merging the attestation with the input provenance.

18. A data processing apparatus according to claim 1, wherein
in response to the input provenance meeting a condition, the management environment is configured to produce the output provenance by outputting the attestation.

19. A data processing apparatus according to claim 18, wherein
the condition comprises a requirement that the input provenance is verified.

20. A data processing apparatus according to claim 1, wherein
the processing environment is configured to process the input data or the output data to generate further output data; and
the output policy is configured to permit forwarding of the further output data in dependence on the output data.

21. A data processing apparatus according to claim 20, wherein
the output policy is configured to permit forwarding of the further output data in dependence on the output data having a given characteristic.

22. A data processing apparatus according to claim 1, wherein
the management environment is provided by a hypervisor; and
the processing environment is a virtual machine that is managed by the hypervisor.

23. A data processing apparatus according to claim 1, wherein
the management environment is configured to control a behavior of the processing environment to operate according to at least one processing policy.

24. A data processing apparatus according to claim 23, wherein
the at least one processing policy comprises a state reset condition; and
in response to the state reset condition being met, the management environment causes a processing state of the processing environment to be reset.

25. A data processing apparatus according to claim 23, wherein
the at least one processing policy comprises a logging condition; and
in response to the logging condition being met, the management environment causes a processing state to perform logging.

26. A data processing apparatus according to claim 23, wherein
the at least one processing policy comprises one or more error handling rules; and
in response to an error condition occurring in the processing environment, the management environment causes the error condition to be handled according to the one or more error handling rules.

27. A data processing apparatus according to claim 1, wherein
an attestation is provided in respect of at least one of the at least one input policy and the at least one output policy.

28. A data processing apparatus according to claim 1, wherein
- at least one of the at least one input policy and at least one output policy comprises a base policy and another policy; and
- the other policy is at least as restrictive as the base policy.

29. A method of data processing comprising:
- receiving input data and an input provenance that relates to the input data;
- forwarding some or all of the input data and the input provenance at an input policy filter according to at least one input policy;
- receiving the input data forwarded by the input policy filter;
- processing the input data to generate output data;
- producing an attestation of the processing environment;
- producing an output provenance based on the input provenance and the attestation; and
- receiving the output data and the output provenance and forwarding the output data and the output provenance according to at least one output policy, wherein
- the input provenance is cryptographically signed, and
- the attestation of the processing environment is cryptographically signed.

\* \* \* \* \*